United States Patent [19]

Pless et al.

[11] 4,187,295

[45] Feb. 5, 1980

[54] ORGANIC COMPOUNDS

[75] Inventors: Janos Pless, Basel; Edmond Sandrin, Riehen, both of Switzerland

[73] Assignee: Sandoz Ltd., Basel, Switzerland

[21] Appl. No.: 940,051

[22] Filed: Sep. 6, 1978

[30] Foreign Application Priority Data

Sep. 7, 1977 [CH] Switzerland .................. 10939/77
Nov. 17, 1977 [CH] Switzerland .................. 14058/77
May 19, 1978 [CH] Switzerland .................. 5468/77

[51] Int. Cl.$^2$ .................. A61K 37/00; C07C 103/52
[52] U.S. Cl. .................. 424/177; 260/112.5 R
[58] Field of Search .................. 260/112.5 R; 424/177

[56] References Cited

U.S. PATENT DOCUMENTS 3,864,481  2/1975  Hashin .................. 260/112.5 R
4,113,858  9/1978  Hashin .................. 260/112.5 R Primary Examiner—Delbert R. Phillips
Attorney, Agent, or Firm—Gerald D. Sharkin; Robert S. Honor; Thomas O. McGovern

[57] ABSTRACT

The invention provides polypeptides useful, for example, as soporifics, a process for the preparation thereof and compositions containing these compounds.

35 Claims, No Drawings

ORGANIC COMPOUNDS

The present invention relates to polypeptide derivatives.

More particularly, the present invention provides compounds of formula I,

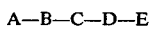

A—B—C—D—E    I wherein
A is H—Trp, H—MeTrp, H—Trp(5—OH) or H—MeTrp(5—OH),
B is Ala,
C is Ser, Thr, Ala, Gly, Val, a residue of formula

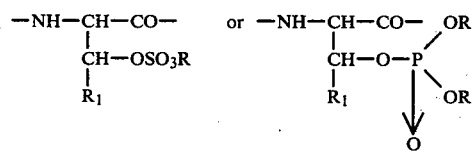

wherein
R is hydrogen, alkyl of 1 to 4 carbon atoms, or an alkali metal or an alkaline earth metal
and
$R_1$ is hydrogen or methyl,
D is Gly or Sar,
E is a residue $$-NH-CH-CH_2-Y,$$
$$\quad\quad\;\; |$$
$$\quad\quad\;\; X$$

wherein
X and Y independently signify COZ or $CH_2OH$,
Z is OH, $OR_2$, $NH_2$, $NHR_3$ or $NR_3R_4$, and
each of $R_2$, $R_3$ and $R_4$ independently signifies alkyl of 1 to 4 carbon atoms
whereby the residues A, B, C and E can have the L-, D- or D, L configuration.

The residue A can, for example, be H—Trp or H—MeTrp. Additionally, A can be H—Trp(5—OH) or H—MeTrp(5—OH).

The residue C can be Ser, Thr, Ala, Gly or Val. Additionally, C can be a residue

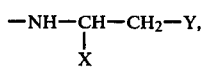

wherein R and $R_1$ are as previously defined. C can also be a residue

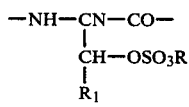

wherein R and $R_1$ are as previously defined.

In one group of compounds R is hydrogen or alkyl of 1 to 4 carbon atoms. In another group of compounds R is an alkali or alkaline earth metal.

The residue E can be a group —NH—CHX—CH$_2$—Y where X and Y are as previously defined. When X and/or Y is/are COZ, Z can be OH or $OR_2$ wherein $R_2$ is as previously defined. Z can also be $NH_2$, $NHR_3$ or $NR_3R_4$ wherein $R_3$ and $R_4$ are as previously defined.

A peptide of formula I can be obtained by methods which are conventional in the art.

Accordingly, the present invention provides a process for the production of a peptide of formula I which comprises,
(a) removing at least one protective group from a protected peptide having the sequence indicated in formula I, or
(b) linking together by an amide bond two peptide units each of which contains at least one amino acid and which is in protected or unprotected form, the peptide units being such that the amino acid sequence given in formula I is obtained, and then, if necessary, effecting process variant a), or
(c) converting a group E of an unprotected or protected peptide into another group E having the definition previously indicated, and, if necessary effecting process variant (a).

The above methods are known in peptide chemistry and may be effected in manner analogous to the processes described in the following Examples.

Insofar as the production of the starting materials is not particularly described, these compounds are known or may be produced and purified in accordance with known methods. These compounds may also be produced in a manner analogous to the processes described in the following Examples.

The compounds may exist in salt form, including acid addition salt forms or in the form of complexes, for example, complexes with metals. Suitable acids for acid addition salt formation include organic acids, polymeric acids and inorganic acids. Complexes may, for example, be formed with elements such as metals, e.g. calcium, magnesium, aluminium, cobalt and especially zinc.

In the following Examples, all temperatures are indicated in degrees Celsius.

The following abbreviations are used:
Asn=asparagine residue
Asnol=asparaginol residue
Asp-diol=asparaginediol-=2-amino-butane-1,4-=diol residue
Asp(NHCH$_3$)-ol=N'-methylasparaginol residue
Asp(OMe)-OMe=aspartic acid dimethyl ester residue
DMF=dimethyl formamide
Et=ethyl
Me=methyl
MeTrp=N-methyltryptophan residue
(5-OH)-Trp=5-hydroxytryptophan residue
OTcp=2,4,5-trichlorophenoxy
TFA=trifluoroacetic acid.
Z=benzyloxycarbonyl All of the amino acid residues with the exception of glycyl, as well as all of the amino alcohol residues referred to in this specification, possess the L—configuration unless otherwise stated. An amino alcohol is associated with the L—series when the CH$_2$OH group is in the same position as the α—COOH group in the corresponding L—amino acid.

EXAMPLE 1: H-Trp-Ala-Ser-Gly-L-Asn-ol

To a solution of 2.0 g of Z-Trp-Ala-Ser-Gly-L-Asn-ol in 80 ml of dioxane and 3.2 ml of aqueous IN HCL is added 1 g of a palladium catalyst and hydrogenation is effected at room temperature and normal pressure until no further hydrogen is taken up. The solution is filtered, the solvent evaporated and the residue is triturated with ether. The resulting title compound in the form of the hydrochloride salt, decomposes at 170°. $[\alpha]_D^{20} = -15.3$ (C=1.0 in water).

The Z-Trp-Ala-Ser-Gly-L-Asn-ol used as starting material is prepared as follows:

(a) Z-Trp-Ala-Ser-Gly-NHNH$_2$ 10.5 g of Z-Trp-OTcp are added to a solution of 6.0 g of H-Ala-Ser-Gly-OEt. hydrochloride and 2.8 ml of triethylamine in 50 ml of DMF. After standing for 24 hours at room temperature the solvent is removed in vacuo and the residue triturated with dilute aqueous HCl and ethyl acetate. The residue is dissolved in 80 ml of DMF and 12 ml hydrazine hydrate are added. After standing for 24 hours the title compound is precipitated by adding ether. The precipitate is filtered, washed with ethanol and dried.

(b) Z-Trp-Ala-Ser-Gly-L-Asn-ol 2.9 ml of 5.6 N HCl in dioxan and 0.67 ml of tert. butyl nitrite are added at $-20°$ to a solution of 3.2 g of Z-Trp-Ala-Ser-Gly-NHNH$_2$ in 50 ml of DMF. After standing 15 minutes at $-20°$ 1.89 of L-Asparaginol hydrochloric and 2.5 ml of triethylamine are added. After standing for 15 hours at room temperature the reaction mixture is considerably reduced in volume, diluted with ethyl acetate and washed with dilute aqueous hydrochloride acid and with water. The title compound precipitates from the concentrated solution.

The following compounds of formula I (wherein D=Gly) can be prepared in manner analogous to that of Example 1 using appropriate starting materials in approximately equivalent amounts.

| Ex. No | A | B | C | E | Salt-form | $[\alpha]_D^{20}$ |
|---|---|---|---|---|---|---|
| 2 | H—Trp | Ala | Ser | Asp—OH | HCl | $-1,0^a$ |
| 3 | H—Trp | Ala | Ser | Asn—OH | HCl | $-16,2^a$ |
| 4 | H—Trp | Ala | Ser | Asn-OMe | HCl | $-17,0^b$ |
| 5 | H—Trp | Ala | Ser | Asp-diol | HCl | $-20,0^b$ |
| 6 | H—Trp | D—Ala | Ser | Asn-ol | HCl | $+14,9^a$ |
| 7 | H—Trp | D—Ala | Ser | Asp—OH | HCl | $-4,6^a$ |
| 8 | H—Trp | D—Ala | Ser | Asn—OH | HCl | $-8,7^a$ |
| 9 | H—Trp | D—Ala | Ser | Asn—OMe | HCl | $-6,3^a$ |
| 10 | H—Trp | D—Ala | Ser | Asp-diol | HCl | $-7,9^a$ |
| 11 | H—D-Trp | Ala | Ser | Asn-ol | HCl | $-86,3^b$ |
| 12 | H—D—Trp | Ala | Ser | Asp—OH | HCl | $-75,7^b$ |
| 13 | H—D—Trp | D—Ala | Ser | Asn-ol | HCl | $-72,4^b$ |
| 14 | H—D—Trp | D—Ala | Ser | Asp—OH | HCl | $-10^b$ |
| 15 | H—MeTrp | Ala | Ser | Asn-ol | TFA | $-10,3^b$ |
| 16 | H—MeTrp | Ala | Ser | Asp—OH | TFA | $-13,5^b$ |
| 17 | H—Trp | Ala | Gly | Asp—OH | HCl | $+17,6^a$ |
| 18 | H—Trp | D—Ala | Thr | Asn-ol | HCl | $+18,7^a$ |
| 19 | H—Trp | D—Ala | Thr | Asp—OH | HCl | $+20,9^a$ |
| 20 | H—Trp | D—Ala | Ser | Asp(OMe)-OMe | HCl | $-2,4^a$ |
| 21 | H—(5-OH)—Trp | D—Ala | Ser | Asp—OH | TFA | $+27,7^a$ |
| 22 | H—Trp | Ala | Val | Asn-ol | HCl | $-1,7^a$ |
| 23 | H—Trp | D—Ala | Gly | Asp—OH | HCl | $+29,8^c$ |
| 24 | H—Trp | D—Ala | Ser | Asp(NHCH$_3$)-ol | HCl | $+18,0^d$ |
| 25 | H—Trp | D—Ala | Val | Asp-diol | HCl | $+16,7^e$ | a: c = 1,0 in 95% acetic acid
b: c = 1,0 in water
c: c = 0,55 in 95% acetic acid
d: c = 0,51 in 95% acetic acid
e: c = 0,96 in 95% acetic acid The compounds of formula I are useful because they possess pharmacological activity in animals. In particular, the compounds possess central nervous system activity. This activity, which is dependent on the structure and dosage of the compound administered, can either suppress or stimulate the central nervous system. The CNS activity is indicated in standard tests in animals, for example by the changes in the spontaneous behaviour in mice and rats, following oral or i.p. application of the compounds. The method (P.O.T.) is described in: S. Irwin, Gordon Research Conference, Medicinal Chemistry, 1959; J.H. Nodide and P.E. Siegler, Animal and Clinical Pharmacologic Techniques in Drug Evaluation, Chicago 1964 and in Psychopharmacologia 13, 222–257, 1968 (Berlin).

These activities can also be demonstrated in mice by means of the Motron test. In this test, the motor activity of the animals is determined electronically using a motility measuring apparatus. For each dose, two groups each comprising five mice (one group as a control group) are set up and the movement as well as the sitting-up activity of the mice are separately determined every fifteen minutes over a period of seventy-five minutes. The E.D.50 and E.D.200 are, respectively, the dosages at which the observed motor activity of the mice is half or twice that of the control animals. Many of the compounds which cause sedation of the mouse can also act as stimulants and the above method permits an evaluation of the chronological differentiation of the two opposed activities on the motor activity of the mouse.

The compounds of formula I are also useful because they possess anti-depressant activity as indicated in standard tests in animals for example in the tetrabenazine antagonism test according to G. Stille [Arzneimittelforschung 14, 534–7 (1964)] in which an antagonism of ptosis and catalepsy induced in rats by tetrabenazine is observed.

From the aforementioned pharmacological tests it can be determined that the following compounds of formula Ia,

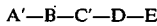

wherein
A' is H-Trp,
and
C' is Gly, Ser,

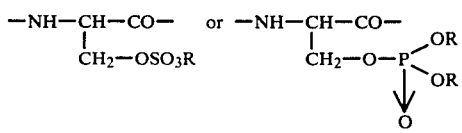

primarily suppress central nervous system activity whereas the remaining compounds of formula I primarily stimulate the central nervous system.

The compounds which suppress CNS activity are useful as sedatives and especially as soporifics, whereas the compounds which stimulate the CNS are useful in the treatment of cerebral insufficiency and depression.

For these uses, the dosage will of course vary depending on the compound employed, mode of administration and treatment desired. However, in general, satisfactory results are obtained when administered at a daily dosage of from about 0.1 to about 100 mg/kg of animal body weight conveniently given in divided doses 2 to 4 times a day or in sustained release form. For the larger mammal, the total daily dosage is in the range of from about 5 to 500 mg and dosage forms suitable for oral administration comprise from about 1.25 to about 250 mg of the compounds admixed with a solid or liquid pharmaceutical carrier or diluent.

The compounds may be administered in pharmaceutically acceptable salt forms including acid addition salt forms, or in the form of complexes. Such forms exhibit the same order of activity as the free base forms and are readily prepared in conventional manner. Representative acids for acid addition salt formation include organic acids, such as trifluoroacetic acid and inorganic acids such as hydrochloric acid. Suitable metals for complex formation include calcium and magnesium.

The present invention also provides a pharmaceutical composition comprising a compound of formula I, in free base form or in the form of a pharmaceutically acceptable salt or complex, in association with a pharmaceutically acceptable carrier or diluent. Such compositions may be in the form of, for example, a solution or capsule.

In one group of compounds A is H—Trp, H-MeTrp, H-Trp(5-OH) or H-MeTrp(5-OH), B is Ala, C is Ser, Thr, Ala, Gly or a residue of formula

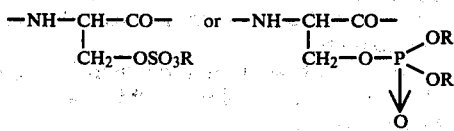

wherein R is hydrogen, alkyl of 1 to 4 carbon atoms an alkali metal or an alkaline earth metal, D is Gly and E is Asp-OH, Asp-OR', Asp-$NH_2$, Asn-OH, Asn-OR', Asn-$NH_2$, asparaginol or a residue of formula

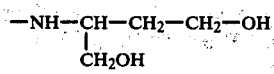

wherein R' is alkyl of 1 to 4 carbon atoms and the residues A, B, C and E have the L-, D- or D, L-configuration.

In a second group of compounds A is H-Trp, H-MeTrp, H-Trp(5-OH) or H-MeTrp, B is Ala, C is Ser, Thr, Ala, Gly or a residue of formula

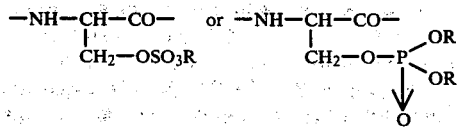

wherein R is hydrogen, alkyl of 1 to 4 carbon atoms, an alkali metal or an alkaline earth metal, D is Gly and E is Asp(OR')-X' wherein R' is alkyl of 1 to 4 carbon atoms and X' is hydroxyl, alkoxy of 1 to 4 carbon atoms or $NH_2$ and the residues A, B, C and Asp(OR')-X' have the L-, D- or D,L-configuration.

What is claimed is:

1. A compound of the formula

A—B—C—D—E                    I wherein

A is H—Trp, H—MeTrp, H—Trp(5—OH) or H—MeTrp(5—OH),

B is Ala,

C is Ser, Thr, Ala, Gly, Val, a residue of formula

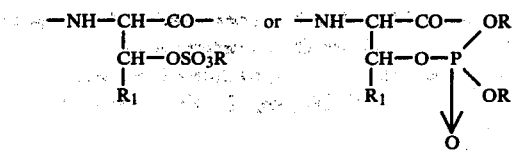

wherein

R is hydrogen, alkyl of 1 to 4 carbon atoms, or an alkali metal or an alkaline earth metal and $R_1$ is hydrogen or methyl, D is Gly or Sar, E is a residue

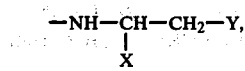

wherein

X and Y independently signify COZ or $CH_2OH$,

Z is OH, $OR_2$, $NH_2$, $NHR_3$ or $NR_3R_4$, and each of $R_2$, $R_3$ and $R_4$ independently signifies alkyl of 1 to 4 carbon atoms whereby the residues A, B, C and E can have the L-, D- or D, L configuration, or a pharmaceutically acceptable salt or complex form thereof.

2. H-Trp-Ala-Val-Gly-Asn-ol.

3. A pharmaceutical composition comprising a compound of claim 1, in association with a pharmaceutically acceptable diluent or carrier.

4. A method of sedating or inducing sleep in animals, which comprises administering to an animal in need of such treatment, a therapeutically effective amount of a compound of claim 1.

5. A method of treating cerebral insufficiency or depression in animals, which comprises administering to an animal in need of such treatment, a therapeutically effective amount of a compound of claim 1.

6. A compound according to claim 1 in which

A is H-Trp, H-MeTrp, H-Trp(5-OH) or H-MeTrp(5-OH),

B is Ala,

C is Ser, Thr, Ala, Gly,

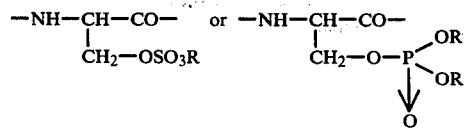

wherein

R is hydrogen, alkyl of 1 to 4 carbon atoms, or an alkali metal or an alkaline earth metal, D is Gly, E is Asp-OH, Asp-OR, Asp-$NH_2$, Asn-OH, Asn-OR', Asn-$NH_2$, asparaginol or $$-NH-CH-CH_2-CH_2-OH,$$
$$\phantom{-NH-}|$$
$$\phantom{-NH-}CH_2OH$$

where
R' is alkyl of 1 to 4 carbon atoms and A, B, C and E have the L-, D- or D,L- configuration.

7. A compound according to claim 1 in which
A is H-Trp, H-MeTrp, H-Trp(5-OH) or H-MeTrp(5-OH),
B is Ala,
C is Ser, Thr, Ala, Gly, $$-NH-CH-CO- \quad \text{or} \quad -NH-CH-CO-$$
$$\phantom{-NH-}| \phantom{CO-xxxxxxxxx} |$$
$$\phantom{-NH-}CH_2-OSO_3R \phantom{xx} CH_2-O-P\begin{smallmatrix}OR\\OR\end{smallmatrix}$$
$$\phantom{xxxxxxxxxxxxxxxxxxxxxxxxxxxx}\downarrow$$
$$\phantom{xxxxxxxxxxxxxxxxxxxxxxxxxxxx}O$$

wherein
R is hydrogen, alkyl of 1 to 4 carbon atoms, or an alkali metal or an alkaline earth metal,
D is Gly, and
E is Asp(OR')-X',
where
R' is alkyl of 1 to 4 carbon atoms and
X' is hydroxyl, alkoxy of 1 to 4 carbon atoms, or NH$_2$ and
A, B, C, and Asp(OR')-X' have the L-, D- or D,L-configuration.

8. The compound of claim 1 in which D is glycine and A, B, C and E are H-Trp, Ala, Ser and Asp-OH, respectively.

9. The compound of claim 1 in which D is glycine and A, B, C and E are H-Trp, Ala, Ser and Asn-OH, respectively.

10. The compound of claim 1 in which D is glycine and A, B, C and E are H-Trp, Ala, Ser and Asn-OMe, respectively.

11. The compound of claim 1 in which D is glycine and A, B, C and E are H-Trp, Ala, Ser and Asp-diol, respectively.

12. The compound of claim 1 in which D is glycine and A, B, C and E are H-Trp, D-Ala, Ser and Asn-ol, respectively.

13. The compound of claim 1 in which D is glycine and A, B, C and E are H-Trp, D-Ala, Ser and Asp-OH, respectively.

14. The compound of claim 1 in which D is glycine and A, B, C and E are H-Trp, D-Ala, Ser and Asn-OH, respectively.

15. The compound of claim 1 in which D is glycine and A, B, C and E are H-Trp, D-Ala, Ser and Asn-OMe, respectively.

16. The compound of claim 1 in which D is glycine and A, B, C and E are H-Trp, D-Ala, Ser and Asp-diol, respectively.

17. The compound of claim 1 in which D is glycine and A, B, C and E are H-D-Trp, Ala, Ser and Asn-ol, respectively.

18. The compound of claim 1 in which D is glycine and A, B, C and E are H-D-Trp, Ala, Ser and Asp-OH, respectively.

19. The compound of claim 1 in which D is glycine and A, B, C and E are H-D-Trp, D-Ala, Ser and Asn-ol, respectively.

20. The compound of claim 1 in which D is glycine and A, B, C and E are H-D-Trp, D-Ala, Ser and Asp-OH, respectively.

21. The compound of claim 1 in which D is glycine and A, B, C and E are H-MeTrp, Ala, Ser and Asn-ol, respectively.

22. The compound of claim 1 in which D is glycine and A, B, C and E are H-MeTrp, Ala, Ser and Asp-OH, respectively.

23. The compound of claim 1 in which D is glycine and A, B, C and E are H-Trp, Ala, Gly and Asp-OH, respectively.

24. The compound of claim 1 in which D is glycine and A, B, C and E are H-Trp, D-Ala, Thr and Asn-ol, respectively.

25. The compound of claim 1 in which D is glycine and A, B, C and E are H-Trp, D-Ala, Thr and Asp-OH, respectively.

26. The compound of claim 1 in which D is glycine and A, B, C and E are H-Trp, D-Ala, Ser and Asp-(OMe)-OMe, respectively.

27. The compound of claim 1 in which D is glycine and A, B, C and E are H-(5-OH)-Trp, D-Ala, Ser and Asp-OH, respectively.

28. The compound of claim 1 in which D is glycine and A, B, C and E are H-Trp, Ala, Ser and L-Asn-ol, respectively.

29. The compound of claim 1 in which D is glycine and A, B, C and E are H-Trp, D-Ala, Gly and Asp-OH, respectively.

30. The compound of claim 1 in which D is glycine and A, B, C and E are H-Trp, D-Ala, Ser and Asp(NHCH$_3$)-ol, respectively.

31. The compound of claim 1 in which D is glycine and A, B, C and E are H-Trp, D-Ala, Val and Asp-diol, respectively.

32. The composition according to claim 3 in which the compound is H-Trp-Ala-Gly-Gly-Asp-OH.

33. The method according to claim 4 in which the compound is H—Trp-Ala-Gly-Gly-Asp-OH.

34. The composition according to claim 3 in which the compound is H-Trp-D-Ala-Ser-Gly-Asp-diol.

35. The method according to claim 4 in which the compound is H-Trp-D-Ala-Ser-Gly-Asp-diol.

* * * * *

UNITED STATES PATENT AND TRADEMARK OFFICE
CERTIFICATE OF CORRECTION

PATENT NO. : 4,187,295
DATED : February 5, 1980
INVENTOR(S) : Janos Pless et al

It is certified that error appears in the above—identified patent and that said Letters Patent is hereby corrected as shown below:

Under the heading "Foreign Application Priority Data", the third entry, after May 19, 1978 [CH] Switzerland . . ., delete "5468/77" and insert -- 5468/78 --.

*Signed and Sealed this*

*Twelfth* Day of *August 1980*

[SEAL]

*Attest:*

*Attesting Officer*

SIDNEY A. DIAMOND

*Commissioner of Patents and Trademarks*